United States Patent
Maurya et al.

(10) Patent No.: US 6,777,392 B2
(45) Date of Patent: Aug. 17, 2004

(54) 8-(C-β-D-GLUCOPYRANOSYL)-7, 3', 4'-TRIHYDROXYFLAVONE, PROCESS OF ISOLATION THEREOF, PHARMACEUTICAL COMPOSITION AND METHOD FOR THE TREATMENT OF DIABETES

(75) Inventors: Rakesh Maurya, Jammu (IN); Sukhdev Swami Handa, Jammu (IN); Rajinder Singh, Jammu (IN)

(73) Assignee: Council of Scientific and Industrial Research, New Delhi (IN)

( * ) Notice: Subject to any disclaimer, the term of this patent is extended or adjusted under 35 U.S.C. 154(b) by 0 days.

(21) Appl. No.: 10/113,204

(22) Filed: Mar. 28, 2002

(65) Prior Publication Data

US 2003/0186898 A1 Oct. 2, 2003

(51) Int. Cl.$^7$ .................. A01K 31/7042; C07H 7/00
(52) U.S. Cl. ............................. 514/27; 536/8
(58) Field of Search ............ 514/27, 456; 536/8; 424/180

(56) References Cited

U.S. PATENT DOCUMENTS 5,886,029 A    3/1999  Dhaliwal ............... 514/456

OTHER PUBLICATIONS

Garcia et al "lavonoids in seed coats of *Medicago arborea* and *M. strasseri* (Leguminosae): Ecophysiological aspects". J. Basic Microbiol., 1992, 32(4), 241–248.*
Bezuindenhoudt et al "Flavonoid Analogues from Pterocarpus Species", Phytochemistry, 26(2), 531–535.*
Garcia, F.P. "Flavonoids in seed coats of *Medicago arborea* and *M. strasseri* (Leguminosae): Ecophysiological aspects", J. Basic Microbiol. vol. 32, no. 4, pp 241–248, 1992.*
Barend C.B. Bezuindenhoudt et al., *Phytochemistry*, 1987, 26(2):531–535.
R. Maurya et al., *J. Natural Prod.*, 1984, 47(1):179–181.
S.K. Jain et al., *Medicinal Plants*, 1968, 116–118.
R.N. Chopra et al., *Indigenous Drugs of India*, 1958, 522.
K.R. Kirtikar et al., *Indian Medicinal Plants*, 1980, 2135–2136.
B.K. Chakravarthy et al., *Lancet*, 1982, 272–273.
H. Kolb et al., *Lancet*, 1982, 1303–04.
B.K. Chakravarthy et al., *Lancet*, 1981, 759–60.
J.S. Dunn et al., *Lancet*, 1943, 384–387.
J.S. Dunn et al., *Lancet*, 1943, 484–487.
FDW Lukenes, *Physiol. Rev.*, 1948, 28:304–330.
B.K. Chakravarthy et al., *Life Sci.*, 1981, 29:2043–2047.
B.K. Chakravarthy et al., *Ind. J. Pharmac.*, 1980, 12:123–127.
E.W. Sheehan et al., *J. Natl Prod.*, 1983, 46(2):232–234.
D.S. Shah, *Ind. J. Med. Res.*, 1967, 55(2):166–168.
S.S. Gupta, *Ind. J. Med. Res.*, 1963, 51(4):716–724.
Padmini Kedar et al., *Maharashtra Med. J.*, 1981, 28(6):165–169.
A. V. Subba Rao et al., *Phytochemistry*, 1982, 21(7):1837–1838.
James Matthew et al., *Phytochemistry*, 1983, 22(3):794–795.
A. V. Subba Rao et al., *Phytochemistry*, 1984, 23(4):897–898.
Subhash C. Jain et al., *Phytochemistry*, 1997, 44(4):765–766.
Dama Adinarayana et al., *Zeitschrift Fur Naturforschung*, 1982, 37C:145–147.
J. Mitra et al., *Phytochemistry*, 1983, 22(10):2326–2327.
Rakesh Maurya et al., *Heterocycles*, 1982, 19(11):2103–2107.
Rakesh Maurya et al., *J. Natural Prod.*, 1984, 47(1):179–181.
Barend C.B. Bezuidenhoudt et al., *Phytochemistry*, 1987, 26(2):531–535.
Dama Adinarayana et al., *Phytochemistry*, 1982, 21(5):1083–1085.
Poonam Mohan et al., *Phytochemistry*, 1989, 28(4):1287–1288.
B.K Chakravarthy et al., *Planta Medica*, 198556–59.

* cited by examiner

Primary Examiner—James O. Wilson
Assistant Examiner—Ganapathy Krishnan
(74) Attorney, Agent, or Firm—Morgan & Finnegan, LLP

(57) ABSTRACT

The present invention relates to a novel compound 8-(C-β-D-glucopyranosyl)-7,3',4'-trihydroxyflavone, isolated from *Pterocarpus marsupium* useful in the treatment of diabetes. The present invention also relates to a method for the preparation of the compound and to the uses thereof.

10 Claims, No Drawings

8-(C-β-D-GLUCOPYRANOSYL)-7, 3', 4'-TRIHYDROXYFLAVONE, PROCESS OF ISOLATION THEREOF, PHARMACEUTICAL COMPOSITION AND METHOD FOR THE TREATMENT OF DIABETES

FIELD OF THE INVENTION

The present invention relates to a novel compound, 8-(C-β-D-glucopyranosyl)-7,3',4'-trihydroxyflavone. The present invention also relates to a process for the isolation of said novel compound 8-(C-β-D-glucopyranosyl)-7,3',4'-trihydroxyflavone from *Pterocarpus marsupium*. The present invention also relates to a pharmaceutical composition containing 8-(C-β-D-glucopyranosyl)-7,3',4'-trihydroxyflavone and to method for the treatment of diabetes using said compound.

BACKGROUND OF THE INVENTION

*Pterocarpus marsupium* Roxb (Legumtnosae) also known as Indian Kino tree or Bijasar, is common in the hilly regions of central and peninsular India [Jain, S. K., Medicinal Plants, National Book Trust, New Delhi, 1968, p. 116]. The extracts of leaves, flowers and gum of this tree have been used medicinally in the treatment of diarrhea, toothache, fever, urinary tract and skin infections. [Chopra, R. N., Chopra, I. C., Handa, K. L. and Kapur, L. D., Indigenous Drugs of India, 2nd Ed., Dhar. U. N. and Sons Private Limited, Calcutta, 1958, p. 522]. The extract of the bark has long been regarded as useful in the therapy of diabetes [Kirtikar, K. R. and Basu, B. D., Indian Medicinal Plants, 2nd Ed., edited by Blatter, E., Cailes, J. F. and Mhaskar, K. S., Singh and Singh, Delhi, India, 1975, p. 2135]. It is reported by Chakravarthy et al [Chakravarthy, B. K., Gupta, S and Gode, K. D., Lancet, 1982, 272 (and references cited therein)] that the active hypoglycemic principle of the bark is (−)-epicatechin and that its effect is due to the regeneration of pancreatic beta cells. However, this claim has been questioned by Kolb et al [Kolb, H., Kiesel, U., Grenlich, B. and Bosch, J. V. D., Lancet, 1982, 1303.] and Sheehan et al [Sheehan, E. W., Zemaitis, M. A., Slatkin, D. J. and Schiff, Jr., P. L., Journal of Natural Products, 1983, 46, 232]. It is now felt that further investigation is necessary before (−)-epicatechin can be considered a viable antidiabetic agent for use in human clinical studies.

Practitioners of the Indian System of Medicine are of the view that the heartwood rather than the bark of *Pterocarpus marsupium* is useful for treatment of diabetic patients and that older the plant more efficacious is its heartwood. It is also claimed that only heartwood that is distinctly red in colour and which imparts a red colouration with bluish green fluorescence to water in which it is kept soaked is suitable for used as an antidiabetic drug.

Hypoglycemic effects of aqueous or alcoholic extracts of heartwood of *Pterocarpus marsupium* have been verified by experimental [Shah, D. S., Indian Journal of Medical Research, 1967, 55, 166 and references cited therein; Gupta, S. S., Indian Journal of Medical Research, 1963, 51, 716] and clinical studies [Sepha, G. C. and Bose, S. N., *J. Ind. Med. Assoc.*, 1956, 27, 383; Ledar, P. and Chkrabarti, C. H., Maharastro Med. J., 1981, 28, 165].

The heartwood of *Pterocarpus marsupium* is rich in phenolics Chemical investigation on heartwood of *P. marsupium* dates back to 1946 by early works [Bhargava, P. N., *Proc. Ind. Acad. Sci.*, 1946, 24A, 496] on this drug are fragmentary in nature. Previous reported studies on this plant disclose the following chemical constituents.

1. Ether extract of *P. marsupium* heartwood furnished isoflavonoid glycol 4,4'-dihydroxy-α-methylhydrobenzoin designated Marsupial [Rao, A. V. S., Mathew, J., *Phytochemistry*, 1982, 21, 1837], a benzofurannone derivative, 2,4',6-trihydroxy-4-methoxybenzo(b)furan-3 (2H)-one designated carpusin [Mathew, J. and Rao, A. V. S.; *Phytochemistry*, 1983, 22, 794], 2-propanol derivative, 1,3-bis (4-hydroxyphenyl)propan-2-ol, designated propterol [Kan, A. V. S., Mathew, J. and Shankaran, A. V. B., *Phytochemistry*, 1984, 23, 897], 1-(2,4-dihydroxyphenyl)-3-(4-hydroxyphenyl)propan-2-ol designated propterol B [Mathew, J., Rao, A. V. S. and Rambbav, S. *Current Science*, 1984, 53, 576], 6-hydroxy-7-O-methyl-3-(3-hydroxy-4-O-methyl benzyl) chroman-4-one [Jain, S. C., Sharman, S. K., Kumar, R, Rajwansh, V. K. and Babu, V. R., *Phytochemistry*, 1997, 44, 765].

2. Hthylacetate soluble fraction of alcoholic extract of heartwood furnished pterosupin β, 2',4,4'-tetrahydroxy-3'(C-β-D-glucopyranoside)dihydrochalcone [Adinarayana, D., Syamsundar, K. V., Seligmann, ( ), & Wagner, H., (Z. Naturforsch, 1982, 37C, 145)], Marsupinol [Trivedi, J. J., *Indian J. Phys. Pharmacol*, 1997, 15, 51], 5,4'-dimethoxy-8-methylisoflavone-7-O-α-L-rhamnopyranoside, restusin-( )-β-D glucopyranoside and irisolidine 7-O-α-L-rhamnopyranoside [Mitra, J. and Joshi, T., *Phytochemistry*, 1982, 21, 2429] and 5,7'-dihydroxy-6-methoxy-7-O-α-L-rhamnopyranoside [Mitra, J. and Joshi, T., *Phytochemistry*, 1983, 22, 2326] obtained from ethylacetate soluble fraction of alcoholic extract of heartwood.

3. Benzofurannone derivative, 2,6-dihydroxy-2-(p-hydroxybenzyl)-4-methoxy-3(2H)-benzofurannone designated as marsupin [Maurya, R., Ray, A. B., Duah, F. K., Slatkin, D. J. & Schiff, P. L. Jr., *Heterocycles*, 1982, 19, 2103] & pterostilbin, (2S)-hydroxyflavone, isoliquiritigein, liquiritigenin, 7,4'-dihydroxyflavone, 5-denoxykaempferol & 3,7,4'-trihydroxyflavone [Maurya, R., Ray, A. B. Duah, F. K., Slatkin, D. J. & Schiff, P. L. Jr., *J. Nat. Prod* 1984, 47, 179], two C-glycoisdes, 8-C-β-D-glucopyranosyl-3,7,4'-trihydroxy & 3,7,3',4'-tetrahydroxyflavone & 3'-C-β-D-glucopyranosyl-α-hydroxy dihydrochalcone [Bezuidenhoudt, B. C. B., Brandt, E. V., and Ferreira, E. V., *Phytochemistry*, 1987, 26, 531] from ethylacetate extract of detatted heartwood.

4. The petrol extract of *P. marsupium* root afforded selin-4(15)-one-1β, 11-diol, β-eudesmol, erythrodiol-3-monoacetac and pterostilbene [Admarayana, D., and Syamasundar, K. V., *Phytochemistry*, 1982, 22, 1083]. Ethanolic extract of *P. marsupium* flowers furnished 4,6,4'-trihydroxyaurone 6-O-rhamnopyranoside and 4,6,4'-trihydroxy-1-methylantrone 4-O-rhamnopyranoside [Mohan, P., and Joshi, T., *Phytochemistry*, 1989, 28, 1287] and ethanolic extract of *P. marsupium* bark furnished (−)-epicatechin [Chakravarthy, B. K., and Gode, K. D., *Planta Medica*, 1985, 56].

However, the prior art does not provide any details about the biological activities associated with such chemical constituents. Also prior art discloses only preparation of ether extract, ethyl acetate extract and ethyl acetate soluble fraction of the alcoholic extract but does not disclose any method of preparing water extracts of heartwood of *Pterocarpus marsupium* and attempting to isolate any chemical constituents therefrom.

OBJECTS OF THE INVENTION

The main object of the invention is to accordingly prepare water extracts of the heartwood of *Pterocarpus marsupium* and to obtain chemical constituents therefrom.

It is another object of the invention to investigate the water extracts of heartwood of *Pterocarpus marsupium* to obtain bioactive fractions useful in the treatment of diabetes.

SUMMARY OF THE INVENTION

The above and other objects of the invention are achieved by preparing a n-butanol soluble water extract of investigate the water extract of heartwood of *Pterocarpus marsupium* and isolating a novel bioactive fraction therefrom. Accordingly, the present invention provides a novel compound 8-(C-β-D-glucopyranosyl)-7,3',4'-trihydroxyflavone.

The present invention also provides a process for the isolation of 8-(C-β-D-glucopyranosyl)-7,3',4'-trihydroxyflavone which comprises:

(a) powdering the heartwood of the plant *Pterocarpus marsupium*, (b) extracting the powdered plant material so prepared with a protic solvent, (c) concentrating the extract to minimum volume and partitioning with different organic solvents of increasing polarity to remove non-polar components, extracting the aqueous layer with polar solvent, removing the solvent to get the residue., (d) isolating the 8-(C-β-D-glucopyranosyl)-7,3',4'-trihydroxyflavone from the residue.

In one embodiment of the invention, the protic solvent used for preparing the extract in step (b) is selected from the group consisting of water, methanol, ethanol, propanol, butanol and any mixture thereof.

In a further embodiment of the invention the polar solvent used to extract the aqueous layer is selected from ethyl acetate, propanol and butanol.

In another embodiment of the invention, organic solvent used in step (c) to remove non-polar components is selected from group consisting of hexane, pet ether and chloroform.

In another embodiment of the invention, the chromatographic methods used for the isolation of 8-(C-β-D-glucopyranosyl) 7,3',4'-trihydroxyflavone is selected from MPLC, HPLC and flash chromatography.

The present invention also relates to a pharmaceutical composition containing a pharmaceutically effective amount of 8-(C-β-D-glucopyranosyl)-7,3',4'-trihydroxyflavone in a pharmaceutically acceptable carrier.

In one embodiment of the invention, the amount of 8-(C-β-D-glucopyranosyl)-7,3',4'-trihydroxyflavone in said composition is in the range of 0.5 mg to 10 mg per kg of body weight of the patient.

The invention also relates to a method for the treatment of diabetes comprising administering a pharmaceutically effective amount of 8-(C-β-D-glucopyranosyl)-7,3',4'-trihydroxyflavone to a patient.

In one embodiment of the invention, the amount of 8-(C-β-D-glucopyranosyl)-7,3',4'-trihydroxyflavone in said composition is in the range of 0.5 mg to 10 mg per kg of body weight of the patient.

The present invention also relates to the use of 8-(C-β-D-glucopyranosyl)-7,3',4'-trihydroxyflavone in preparation of a pharmaceutical composition for treatment of diabetes.

DETAILED DESCRIPTION OF THE INVENTION

The present invention provides a process for the isolation of 8(C-β-D-glucopyranosyl)-7,3',4'-trihydroxyflavone which comprises:

(a) powdering the heartwood of the plant *Pterocarpus marsupium*, (b) extracting the powdered plant material so prepared with a protic solvent, (c) concentrating the aqueous extract to minimum volume and partitioning with organic solvents of increasing polarity to remove non-polar components, extracting the aqueous layer with polar solvent, removing the solvent to get the residue.

(d) isolating the 8-(C-β-D-glucopyranosyl)-7,3',4'-trihydroxyflavone from residue.

The solvent used for preparing the extract may be water, methanol, ethanol, propanol and butanol and like or their mixtures. The organic solvent used in step (c) to remove the non-polar components is selected from the group consisting of hexane, pet ether and chloroform. The polar solvent used to extract the aqueous layer is selected from ethyl acetate, propanol and butanol. The chromatographic methods used for the isolation of 8-(C-β-D-glucopyranosyl)-7,3',4'-trihydroxyflavone may be MPLC, flash chromatography etc.

In the MPLC method the required eluting solvent is pumped through the column and in the flash chromatography solvent is pushed with air pressure. The compound was assigned the molecular formula $C_{21}H_{20}O_{10}$ [FAB-MS, m/z 433[M+1]$^+$]. This conclusion was supported by $^{13}$CNMR and DEPT spectra.

The compound 8-(C-β-D-glucopyranosyl)-7,3',4'-trihydroxyflavone was isolated from the n-butanol soluble fraction of the water decoction of the heartwood of *P. marsupium* which has shown antidiabetic activity in both humans and animals. There is no disclosure in the prior art of this compound since work had been done in the art on the ether extract, ethyl acetate extract and ethyl acetate soluble fraction of the alcoholic extract.

The process of isolating active principle from *Pterocarpus marsupium* comprises partition of the aqueous extract of powdered heartwood with different organic solvents containing 1–6 carbon atoms in the molecule. 8-(C-β-D-glucopyranosyl)-7,3',4'-trihydroxyflavone is isolated from polar fraction by applying modern chromatographic techniques such as medium pressure liquid chromatography (MPLC), high pressure liquid chromatography (HPLC) and flash chromatography using silica gel (230 400 mesh) and shows hypoglycaemic activity.

The compound 8-(C-β-D-glucopyranosyl)-7,3',4'-trihydroxyflavone has been evaluated for hypoglycaemic activity in 18 h. fasted Wistar rats. In the dose of 10 mg/kg p. o., hypoglycaemic effect was recorded in all the treated rats. The mean fall recorded was 24 mg/100 ml. blood, from initial mean of 92 to mean of 68 mg/100 ml. blood. As compared to this, the clinically used hypoglycaemic agent, employed as positive control in the study, showed mean fall of 23 mg/100 ml. blood.

The compound was proved to be a phenol from its positive phosphomolybedic acid test (blue), ferric chloride test (green) It was recognized to be a flavone as it responded to the Shinoda test. The presence of hydroxy, carbonyl, and phenyl nucleus was indicated by the IR absorption at 3228, 1615, 1554, 1448, 1422 cm$^{-1}$. The UV spectrum of the compound showed absorption maxima at $\lambda_{max}^{MeOh}$ 219, 238, 260, 320, 358 nm which underwent bathochromic shift 219, 238, 267, 320, 367 nm is presence of NaOAc. This observation suggested the presence of a free hydroxyl group located at C-7.

The $^1$H NMR spectrum (200 MHz, in DMSO-d$_6$) displayed broadening of signals in the aromatic regions presumably because of the steric crowding of the glucosyl and B-ring. The inspection of spectrum revealed in singlet signal at δ 6.98 (1H) characteristic of proton at C-3 of flavone. A doublet proton signal at δ 8.28 (1H, d, J=2.1 Hz) which is low field shifted due to the effect of the neighbouring C=O, is ortho-coupled with the doublet signal at δ 6.95 (1H, d, J=8.3 Hz). This ortho coupling is assigned to the proton at C-5 and C-6 indicating that only these two protons belong to A ring and that C-8 is occupied by a glucosyl group. The proton signal at δ 7.81 (1H, br d, J=2.1 Hz), 797 (1H, br dd, J=2.1, 8 7 Hz) and 6.99 (1H, d, J=8 7 Hz) are assigned to the protons at the B-ring. Further $^1$H and $^{13}$C NMR spectra showed signals attributed to one glucose moiety. The C—C coupling was exemplified by $^1$H and $^{13}$C heteronuclear correlation of the anomeric proton at δ 5.16 with a carbon doublet at δ 79.3 in the region characteristic of $C_1$-substituted glucosides. Further the coupling constant (J=9.5 Hz) of the signal resulting from the anomeric proton of the glucopyranoside indicated that the flucosidic linkage has β-configuration. Thus the above analysis led to the structure 8-(C-β-D-glucopyranosyl)-7,3',4'-trihydroxyflavone.

The invention is described in detail by the examples given below which should not be construed to the limit of scope of the present invention.

EXAMPLE 1

The powdered heartwood of Pterocarpus marsupium (1 kg) was percolated with 80% aqueous ethanol (3×3 lits.) for a period of 48 hours. The resultant concentrate was partitioned with hexane, chloroform, propanol and butanol in the order. The polar extract was subjected to MPLC using silica gel (100–200 mesh) for gross fractions with hexane, chloroform, methanol, ethanol in that order. The active compound was purified by repeated MPLC and flash chromatography over silica gel (230–400 mesh) using CHCl$_3$—MeOH (19:1) as solvent to furnish 8-(C-β-D-glucopyranosyl)-7,3',4'-trihydroxyflavone, (yield 0.046) mp. 202–204° C., $[α]_D^{19}$+25.6° (MeOH, c, 0.5).

EXAMPLE 2

The heartwood of Pterocarpus marsupium was extracted with hot water for a period of 4×4 hours. The resultant concentrate was partitioned between hexane, chloroform, propanol and butanol in that order. The polar extract so obtained was subjected to flash chromatography employing silica gel (100–200 mesh) using hexane, chloroform, ethylacetate and methanol as solvent system to afford 8-(C-β-D-glucopyranosyl)-7,3',4'-trihydroxyflavone rich fraction, which on repeated chromatography over silica gel (230–400 mesh) using EtOAc—MeOH (19.5:0.5) as solvent, furnished 8-(C-β-D-glucopyranosyl)-7,3',4'-trihydroxyflavone of the formula 1 (yield 0.049%, mp. 202–204° C., $[α]_D^{19}$+25.6° 1 (MeOH, c, 0.5).

EXAMPLE 3

The heartwood of Pterocarpus marsupium was boiled with water (16 times) till ¼ volume of water is left. Filtered, concentrated and partitioned between hexane, chloroform, ethyl acetate, propanol and n-butanol in that order. The polar extract obtained was subjected to column chromatography employing silica gel (60–120 mesh) using hexane, chloroform, ethyl acetate and methanol as solvent system to afford 8-(C-β-D-glucopyranosyl)-7,3',4'-trihydroxyflavone rich fraction. The 8-(C-β-D-glucopyranosyl)-7,3',4'-trihydroxyflavone rich fraction on repeated column chromatography over silica gel (100–200 mesh) using mixture of ethyl acetate—acetone (8:2), furnished 8-(C-β-D-glucopyranosyl) 7,3',4'-trihydroxyflavone (yield 0.051%), mp. 202–204° C., $[α]_D^{19}$+25.6° (MeOH, c, 0.5).

Advantages:

1. The compound obtained 8-(C-β-D-glucopyranosyl)-7, 3',4'-trihydroxyflavone is a novel molecule with antidiabetic activity.

2. The method of isolation of 8-(C-β-D-glucopyranosyl)-7,3',4'-trihydroxyflavone is comparatively simple.

We claim:

1. 8-(C-β-D-glucopyranosyl)-7,3',4'-trihydroxyflavone isolated from Pterocarpus marsupium.

2. A process for the isolation of 8-(C-β-D-glucopyranosyl)-7,3',4'-trihydroxyflavone comprising the steps:

(a) powdering the heartwood of the plant Pterocarpus marsupium, (b) extracting the powdered plant material so prepared with a protic solvent;

(c) concentrating the extract to remove a part of the protic solvent and partitioning with different organic solvents of increasing polarity to remove non-polar components, extracting the protic solvent layer with a polar solvent, and removing the polar solvent to obtain a residue; and (d) isolating the 8-(C-β-D-glucopyranosyl)-7,3',4'-trihydroxyflavone from the residue.

3. A process according to claim 2 wherein the protic solvent used in step (b) is selected from the group consisting of water, methanol, ethanol, butanol and any mixture thereof.

4. A process according to claim 2 wherein the organic solvent used in step (c) to remove the non-polar components is selected from the group consisting of hexane, petroleum ether and chloroform.

5. A process according to claim 2 wherein the polar solvent used to extract the aqueous layer is selected from the group consisting of ethyl acetate, propanol and butanol.

6. A process according to claim 2 wherein in step d) the residue is dissolved in a polar solvent and a chromatographic method is employed to isolate 8-(C-β-D-glucopyranosyl)-7, 3',4'-trihydroxyflavone and the chromatographic method is selected from the group consisting of medium pressure liquid chromatography (MPLC), high pressure liquid chromatography (HPLC) and flash chromatography.

7. A pharmaceutical composition comprising 8-(C-β-D-glucopyranosyl)-7,3',4'-trihydroxyflavone in a pharmaceutically acceptable carrier.

8. A pharmaceutical composition according to claim 7 wherein the amount of 8-(C-β-D-glucopyranosyl)-7,3',4'-trihydroxyflavone in said composition is as administered to a patient is in the range of 0.5 mg to 10 mg per kg of body weight of the patient.

9. A method for the treating diabetes comprising administering a pharmaceutically effective amount of 8-(C-β-D-glucopyranosyl)-7,3',4'-trihydroxyflavone to a patient in need thereof.

10. A method according to claim 9 wherein the amount of 8-(C-β-D-glucopyranosyl)-7,3',4'-trihydroxyflavone in said pharmaceutical composition is in the range of 0.5 mg to 10 mg per kg body weight of the patient.

* * * * *